(12) United States Patent
Halbach et al.

(10) Patent No.: US 9,309,358 B2
(45) Date of Patent: Apr. 12, 2016

(54) CROSSLINKABLE SILOXANES BY ACID-CATALYZED POLYMERIZATION OF OXASILACYCLES

(71) Applicant: Wacker Chemie AG, Munich (DE)

(72) Inventors: Tobias Halbach, Munich (DE); Juergen Stohrer, Pullach (DE); Bernhard Rieger, Elchingen (DE); Christian Anger, Munich (DE)

(73) Assignee: WACKER CHEMIE AG, Munich (DE)

( * ) Notice: Subject to any disclaimer, the term of this patent is extended or adjusted under 35 U.S.C. 154(b) by 0 days.

(21) Appl. No.: 14/413,558

(22) PCT Filed: Jul. 2, 2013

(86) PCT No.: PCT/EP2013/063926
§ 371 (c)(1),
(2) Date: Jan. 8, 2015

(87) PCT Pub. No.: WO2014/009205
PCT Pub. Date: Jan. 16, 2014

(65) Prior Publication Data
US 2015/0175749 A1    Jun. 25, 2015

(30) Foreign Application Priority Data

Jul. 11, 2012 (DE) .......................... 10 2012 013 710

(51) Int. Cl.
 C08G 77/20 (2006.01)
 C08G 77/04 (2006.01)
 C08L 83/04 (2006.01)
 C07F 7/18 (2006.01)

(52) U.S. Cl.
 CPC .............. *C08G 77/04* (2013.01); *C07F 7/1868* (2013.01); *C08G 77/20* (2013.01); *C08L 83/04* (2013.01)

(58) Field of Classification Search
None
See application file for complete search history.

(56) References Cited

U.S. PATENT DOCUMENTS

| | | | |
|---|---|---|---|
| 4,528,389 A | 7/1985 | Farnham | |
| 5,274,053 A * | 12/1993 | Kurata | C08F 283/12 525/479 |
| 5,786,493 A | 7/1998 | Rauleder et al. | |
| 2001/0011120 A1* | 8/2001 | Okawa | C07F 7/0874 528/10 |
| 2004/0073031 A1 | 4/2004 | Schafer et al. | |
| 2006/0040897 A1* | 2/2006 | Friedman | A61K 31/695 514/63 |
| 2007/0055036 A1 | 3/2007 | Nagy | |
| 2009/0050020 A1* | 2/2009 | Konno | G03F 7/0751 106/287.12 |
| 2009/0298980 A1* | 12/2009 | Yoshitake | C08K 5/50 524/154 |
| 2010/0331483 A1 | 12/2010 | Briehn et al. | |
| 2012/0220793 A1 | 8/2012 | Daiss et al. | |
| 2013/0018200 A1 | 1/2013 | Daiss et al. | |
| 2013/0078333 A1* | 3/2013 | Kumazawa | B29C 33/3878 425/470 |
| 2013/0345370 A1* | 12/2013 | Ona | C07F 7/087 525/477 |

FOREIGN PATENT DOCUMENTS

| | | |
|---|---|---|
| DE | 19628588 A1 | 1/1998 |
| DE | 10109842 A1 | 10/2002 |
| DE | 102004029259 A1 | 1/2006 |
| DE | 102006048217 A1 | 4/2008 |
| DE | 102008000353 A1 | 8/2009 |
| DE | 102009046254 A1 | 5/2011 |
| DE | 102010003108 A1 | 9/2011 |
| EP | 0110370 B1 | 6/1984 |
| EP | 0629648 A2 | 12/1994 |
| JP | 7-149901 | 6/1995 |
| JP | 2000186103 A | 7/2000 |
| WO | 03014167 A1 | 2/2003 |
| WO | 2005044828 A1 | 5/2005 |
| WO | 2011051108 A1 | 5/2011 |

OTHER PUBLICATIONS

W. Noll, "Chemie und Technologie der Silicone," Verlag Chemie GmbH, 1968, pp. 9 (and Abstract).
S. Denmark et al, "A Stereochemical Study on the Intramolecular Hydrosilylation of a,ss-Unsaturated Esters," Tetrahedron Letters, vol. 33, No. 35, pp. 5037-5040, 1992.
R. Shchepin et al, "B(C6F5)3-Promoted Tandem Silyltation and Intramolecular Hydrosilylation: Diastereoselective Synthesis of Oxasilinanes and Oxaselepanes", Organic Letters, 2010 vol. 12, pp. 4772-4775.
X. Baopei et al., "Spiro(benzoxasilole) Catalyzed Polymerization of Oxetane Derivatives", Journal of Polymer Science, Part A: Polymer Chemistry, 30(0), 1899-909 Coden: JPACEC; ISSN 0887-624X; 1992, XP0027-12461.
E.T. Denisov et al., "Handbook of Free Radical Initiators," published by John Wiley & Sons, Inc., 2003.

* cited by examiner

*Primary Examiner* — Robert S Loewe
(74) *Attorney, Agent, or Firm* — Brooks Kushman P.C.

(57) ABSTRACT

Compounds of the general formula (4) are prepared by polymerization of oxasilacycles in the presence of an acid catalyst.

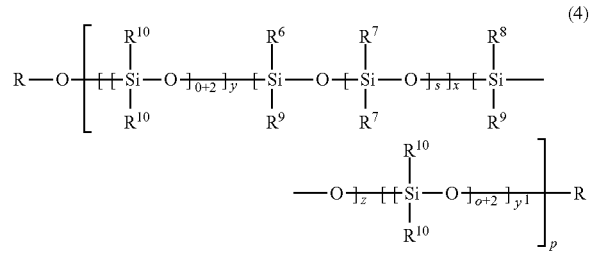

24 Claims, No Drawings

CROSSLINKABLE SILOXANES BY ACID-CATALYZED POLYMERIZATION OF OXASILACYCLES

CROSS REFERENCE TO RELATED APPLICATIONS

This application is the U.S. National Phase of PCT Appln. No. PCT/EP2013/063926 filed 2 Jul. 2013, which claims priority to German Application No. 10 2012 013 710.9 filed Jul. 11, 2012, the disclosures of which are incorporated in their entirety by reference herein.

BACKGROUND OF THE INVENTION

1. Field of the Invention

The invention relates to crosslinkable siloxanes by acid-catalyzed polymerization and copolymerization of oxasilacycles.

2. Description of the Related Art

DE102008000353A1 describes crosslinkable polymer blends containing at least one alkoxysilyl group $\equiv$Si—O—C($R^1$)($R^2$)($R^3$) and their use for water-free silane crosslinking.

Cyclic siloxanes such as hexamethylcyclotrisiloxane or octamethylcyclotetrasiloxane can be polymerized by catalysis using Lewis or Brönsted acids to give linear, long-chain siloxanes, as disclosed in, for example, W. Noll, Chemie and Technologie der Silicone, Verlag Chemie GmbH, Weinheim, 1968.

The reaction of cyclic silyl ethers, known as oxacycles, with α,ω-SiOH-terminated polydimethylsiloxanes leads to carbinol-functional siloxanes, as described in, for example, DE10109842, EP629648, DE102004029259 or DE102009046254.

JP2000186103A describes siloxanes which have a —R—C(CH$_3$)=CH$_2$ side group and are used as monomers in a suspension polymerization in order to produce toner particles.

Polysiloxanes which bear two alkyl radicals having a terminal double bond on some or all siloxane units are unknown to date.

The invention provides a process for the polymerization of oxasilacycles which are selected from among the general formulae (1) and (5)

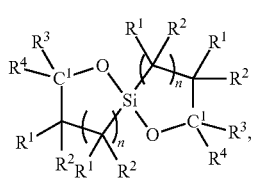  (1)

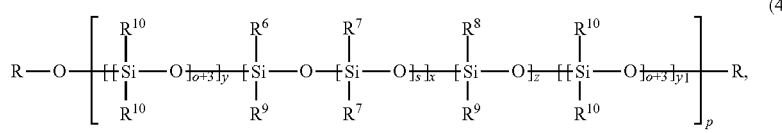  (5)

wherein the oxasilacycles which are selected from among the general formulae (1) and (5) and optionally siloxanes which are selected from among linear siloxanes of the general formula (3) and cyclic siloxanes of the general formula (3a)

$$RO-Si(R^7)_2O[Si(R^7)_2O]_oSi(R^7)_2-OR,\quad (3)$$

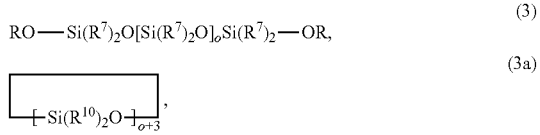  (3a)

are polymerized in the presence of acid catalyst K to form compounds of the general formula (4)

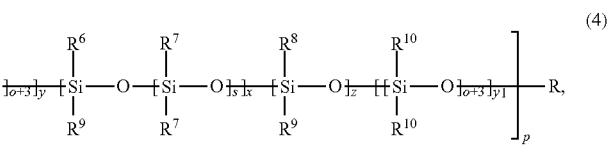  (4)

where

R is hydrogen, an unsubstituted or substituted hydrocarbon radical or acyl radical, in each case having from 1 to 50 carbon atoms, $R^1$, $R^2$, $R^{1'}$, $R^{2'}$, $R^{1''}$, $R^{2''}$ are each hydrogen, halogen, cyano, OH or an unsubstituted or substituted hydrocarbonoxy radical, acyloxy radical, alkoxy radical or hydrocarbon radical in each case having from 1 to 50 carbon atoms, in which in each case nonadjacent carbon atoms can be replaced by heteroatoms selected from among N, O, P, S, where two or three of the radicals $R^1$, $R^2$, $R^{1'}$, $R^{2'}$, $R^{1''}$, $R^{2''}$ can be joined to one another, $R^3$, $R^4$, $R^{3'}$, $R^{4'}$, $R^{3''}$ are each an unsubstituted or substituted hydrocarbon radical in each case having from 1 to 50 carbon atoms, in which in each case nonadjacent carbon atoms can be replaced by heteroatoms selected from among N, O, P, S, or a high molecular weight radical, $R^{4''}$ is hydrogen, an unsubstituted or substituted hydrocarbon radical in each case having from 1 to 49 carbon atoms, in which in each case nonadjacent carbon atoms can be replaced by heteroatoms selected from among N, O, P, S, or a high molecular weight radical, $R^6$ is an unsubstituted or substituted hydrocarbon radical in each case having from 1 to 50 carbon atoms, in which in each case nonadjacent carbon atoms can be replaced by heteroatoms selected from among N, O, P, S, $R^7$, $R^{10}$ are each an unsubstituted or substituted hydrocarbon radical in each case having from 1 to 10 carbon atoms, $R^8$ is a radical $R^6$ or $R^9$, $R^9$ is a radical of the general formula (6)

$$R^9 = \begin{array}{c} R^{1''} \\ | \\ -\!\!\!\!-\!\!\!\!\!\left[C\right]_{\!n''}\!\!\!\!-\!\!\!\!C\!\!\!\!-\!\!\!\!C \\ | \\ R^{2''} \end{array} \begin{array}{c} R^{1''} \\ | \\ C\!\!\!\!-\!\!\!\!C \\ | \\ R^{2''} \end{array} \begin{array}{c} R^{4''} \\ \diagdown \\ CH, \\ \diagup \\ R^{3''} \end{array} \quad (6)$$

n, n', n" are integers of at least 1,
x, y, $y^1$ are each 0 or 1,
z is an integer of at least 1,
o is an integer of at least 0,
p is an integer of at least 1 and
s is an integer of at least 1.

The oxasilacycles of the general formulae (1) and (5) contain an Si—O—C bond in which the C atom is tetrasubstituted.

In a subsequent step, the compounds of the general formula (4), in particular when R is hydrogen or an acyl radical, are preferably reacted with an end-group-forming compound of the general formula X-EG to give compounds of the general formula (7)

$$EG\!-\!O\!-\!\!\left[\!\!\left[\!\!\begin{array}{c}R^{10}\\|\\Si\!-\!O\\|\\R^{10}\end{array}\!\!\right]_{[o+3]y}\!\!\!\!\begin{array}{c}R^6\\|\\Si\!-\!O\\|\\R^9\end{array}\!\!\left[\!\!\begin{array}{c}R^7\\|\\Si\!-\!O\\|\\R^7\end{array}\!\!\right]_s\!\!\!\!\begin{array}{c}R^8\\|\\Si\!-\!O\\|\\R^9\end{array}\!\!\left[\!\!\begin{array}{c}R^{10}\\|\\Si\!-\!O\\|\\R^{10}\end{array}\!\!\right]_{[o+3]y}\!\!\right]_p\!\!-\!EG, \quad (7)$$

where
X is OH or halogen and
EG is a hydrocarbon or silyl group and
$R^{1''}$, $R^{2''}$, $R^{3''}$, $R^{4''}$, $R^6$, $R^7$, $R^{10}$, $R^8$, $R^9$, n", x, y, $y^1$, z, o, p and s have the meanings given for the general formula (4).

Siloxanes of the general formula (4) can be prepared by means of the process, either by acid-catalyzed ring opening and polymerization of oxasilacycles of the general formula (1) or copolymerization of oxasilacycles of the general formulae (1) and (5) with hydroxy-terminated polydimethylsiloxanes of the general formula (3) or copolymerization of oxasilacycles of the general formulae (1) and (5) and cyclic siloxanes or polymerization of telechelic compounds of the general formula (5) prepared by reaction of siloxanes with oxasilacycles. The siloxanes mentioned can be end-capped to give siloxanes of the general formula (7).

The oxasilacycles of the general formula (5) can be prepared by reaction of the compounds of the general formula (2)

$$\begin{array}{c} R^{3'} \\ R^{4'} \diagdown \diagup \\ C^1\!\!-\!O \quad OR^5, \\ \diagup \quad \diagdown \diagup \\ R^{1'} \quad Si \\ \diagup \quad \diagdown \\ R^{2'} \quad R^6 \\ R^{1'} \quad R^{2'} \end{array} \quad (2)$$

with siloxanes of the general formula (3), where
$R^5$ is an unsubstituted or substituted hydrocarbon radical in each case having from 1 to 10 carbon atoms and
$R^{1'}$, $R^{2'}$, $R^{3'}$, $R^{4'}$, $R^6$ and n are as defined for the general formula (5).

An example of cyclic silanes of the general formula (1) is 2,2,8,8-tetramethyl-1,7-dioxa-6-silaspiro[5.5]undecane and one of the general formula (2) is 2-isopropoxy-2,6,6-trimethyl-1,2-oxasilinane (2).

The siloxanes of the general formulae (4) and (7) in which x, y and $y^1$=0, z=at least 2 and $R^8$ has the same meaning as $R^9$ are novel, fully alkenyl-substituted polysiloxanes which bear two alkyl radicals having a terminal double bond on each siloxane unit. An example of this is the polymerization of 2,2,8,8-tetramethyl-1,7-dioxa-6-silaspiro[5.5]undecane using diphenyliodonium triflate or triphenylsulfonium triflate as catalyst under irradiation with UV light.

Copolymerization of the cyclic silanes of the general formula (1) with linear siloxanes of the general formula (3) and/or with cyclic siloxanes of the general formula (3a) by means of catalysts K forms structures of the general formula (4) in which x=0, y and/or $y^1$=1, z=at least 1 and $R^8$ has the same meaning as $R^9$.

These can be random copolymers or block copolymers having any end group EG.

An example of this is the copolymerization of 2,2,8,8-tetramethyl-1,7-dioxa-6-silaspiro[5.5] having short-chain hydroxyl-terminated polydimethylsiloxanes having a chain length of 15-60 units using diphenyliodonium triflate or triphenylsulfonium triflate as catalyst under irradiation with UV light.

Siloxanes of the general formulae (4) and (7) in which x and z=1 and y and $y^1$=0 and $R^8$ has the same meaning as $R^6$ can be prepared by polymerization of siloxanes of the general formula (5).

All homopolymerizations and copolymerizations give structures having a defined number of double bonds, which can be set via the monomer ratios.

The ring opening and subsequent polymerization is characterized by no volatile organic compounds (VOC) being eliminated.

In the polymerization of the compounds of the general formulae (1) and/or (5) with addition of siloxanes of the general formulae (3) and/or (3a), only water is formed.

If linear siloxanes of the general formula (3) are used for the copolymerization, all linear siloxanes, SiR-end-functionalized silicone oils, and preferably SiOH-functional silicone oils, are suitable. o is preferably from 1 to 100, more preferably from 2 to 50, in particular from 5 to 30.

If cyclic siloxanes of the general formula (3a) are used for the copolymerization, all cyclic siloxanes, preferably cyclic siloxanes in which o=3-10, most preferably cyclic siloxanes in which o=3-5, are suitable.

If linear siloxanes of the general formula (3) and/or cyclic siloxanes of the general formula (3a) are used for the copolymerization, preference is given to using from 0.5 to 3 mol, more preferably from 0.8 to 2 mol, and in particular from 0.9 to 1.2 mol, of siloxanes per mole of oxasilacycles selected from among the general formulae (1) and (5).

The unsubstituted or substituted hydrocarbonoxy radicals, acyloxy radicals or hydrocarbon radicals in each case preferably have from 1 to 12 carbon atoms, in particular from 1 to 6 carbon atoms. Particularly preferred hydrocarbonoxy radicals are methoxy, ethoxy and propoxy, and a particularly preferred acyloxy radical is acetoxy. Examples of hydrocarbon radicals are alkyl radicals such as the methyl, ethyl, n-propyl, isopropyl, 1-n-butyl, 2-n-butyl, isobutyl, tert-butyl, n-pentyl, isopentyl, neopentyl, and tert-pentyl radicals; hexyl radicals such as the n-hexyl radical; heptyl radicals such as the n-heptyl radical; octyl radicals such as the n-octyl radical and isooctyl radicals such as the 2,2,4-trimethylpentyl radical; nonyl radicals such as the n-nonyl radical; decyl radicals such as the n-decyl radical; dodecyl radicals such as the n-dodecyl radical; octadecyl radicals such as the n-octadecyl radical; cycloalkyl radicals such as the cyclopentyl, cyclohexyl, cycloheptyl and methylcyclohexyl radicals; aryl radicals such as the phenyl, naphthyl, anthryl and phenanthryl radicals; alkaryl radicals such as the o-, m-, p-tolyl radicals, xylyl radicals and ethylphenyl radicals; and aralkyl radicals such as the benzyl radical, the α-phenylethyl radical, and the β-phenylethyl radical.

The substituents on the hydrocarbon radicals R, $R^1$, $R^2$, $R^{1'}$, $R^{2'}$, $R^{1''}$, $R^{2''}$, $R^3$, $R^4$, $R^{3'}$, $R^{4'}$, $R^{3''}$, $R^{4''}$, $R^6$, $R^7$, $R^{10}$ can be for example, halogens such as fluorine, chlorine or bromine or cyano radicals.

The radicals $R^3$, $R^{3''}$, $R^{3'}$, $R^4$, $R^{4'}$ preferably have from 1 to 12, in particular from 1 to 6, carbon atoms. Preference is likewise given to high molecular weight radicals which preferably have (polymeric) repeating units.

The radical $R^{4''}$ is preferably hydrogen or a hydrocarbon radical preferably having from 1 to 12, and in particular, from 1 to 6 carbon atoms.

The radicals $R^3$, $R^{3''}$, $R^{3'}$, $R^4$, $R^{4'}$ are most preferably methyl, ethyl, propyl, butyl, vinyl, phenyl or carboxyl radicals —C(O)OCH$_3$.

The radical $R^{4''}$ is more preferably hydrogen, methyl, ethyl, propyl, butyl, vinyl, phenyl or carboxyl radicals —C(O)OCH$_3$. $R^{4''}$ is most preferably hydrogen.

The rings in the oxasilacycles of the general formulae (1) and (2) are at least a 5-membered ring (n, n'=1), preferably a 6- or 7-membered ring (n, n'=2, 3).

The oxasilacycles of the general formulae (1) and (2) have either one ring (formula (2)) or two rings (formula (1)). Oxasilacycles of the general formula (2) preferably have at least one OR$^5$ group in which R$^5$ is preferably an alkyl or aryl group. R$^6$ is preferably an alkyl, acyl or aryl group such as methyl, ethyl, propyl, phenyl, acetoxy, methoxy or ethoxy.

The hydrocarbon radicals $R^7$, $R^{10}$ are preferably unsubstituted. The hydrocarbon radicals $R^7$, $R^{10}$ each preferably have, in particular, from 1 to 6 carbon atoms, with particular preference being given to methyl and phenyl radicals.

The oxasilacycles of the general formula (1) can be prepared by reaction of compounds of the general formula (8)

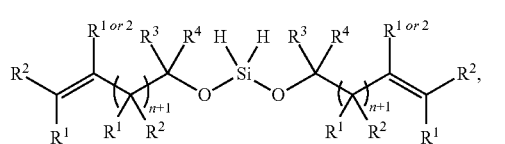

(8)

in the presence of hydrosilylation catalysts.

The oxasilacycles of the general formula (2) can be prepared by reaction of compounds of the general formula (9)

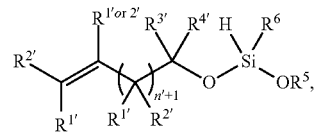

(9)

in the presence of hydrosilylation catalysts.

The preparation of oxasilacycles of the general formulae (1) or (2) occurs via intramolecular hydrosilylation and can be carried out using hydrosilylation catalysts known to those skilled in the art. Preference is given to using platinum metals or compounds thereof or triorganoboranes BR$_3$ or aminoborane complexes R$_3$NBH$_3$ or phosphinoboranes R$_3$PBH$_3$, where R is an unsubstituted or halogen-substituted hydrocarbon radical in each case having from 1 to 12 carbon atoms, as catalyst.

Preferred catalysts (K) are Lewis acids and Brönsted acids. Examples of suitable Lewis acids are tin, tin oxide and tin compounds such as dibutyltin dilaurate (DBTL), titanium, titanium oxide and titanium compounds such as titanium(IV) isopropoxide, Ti(IV) acetylacetonate, copper, copper oxide and copper compounds such as copper(I) trifluoromethanesulfonate, iron, iron oxide and iron compounds such as iron (III) chloride, iron(III) acetylacetonate, manganese, manganese oxide and manganese compounds such as manganese(II) acetylacetonate, aluminum, aluminum oxide and aluminum compounds such as aluminum(III) chloride, aluminum(III) isopropoxide, trimethylaluminum, boron, boron oxide and boron compounds such as boron trichloride, zirconium, zirconium oxide and zirconium compounds such as Zr(IV) acetylacetonate, gallium, gallium oxide and gallium compounds, e.g. gallium(III) acetylacetonate, cerium, cerium oxide and cerium compounds such as cerium(III) chloride and zinc, zinc oxide and zinc compounds such as zinc laurate and zinc pivalate.

Examples of suitable Brönsted acids are carboxylic acids such as lauric acid, sulfonic acids such as trifluoromethanesulfonic acid, p-toluenesulfonic acid and dodecylbenzenesulfonic acid, mineral acids such as hydrochloric acid, nitric acid and phosphoric acid.

Preference is also given to compounds which decompose to generate a Brönsted acid on irradiation with high-energy radiation, for example UV light or electron beam. Examples of such compounds are diaryliodonium compounds such as {4-[(2-hydroxytetradecyl)oxy]phenyl}phenyliodonium hexafluoroantimonate, diphenyliodonium nitrate, bis(4-tert-butylphenyl)-iodonium p-toluenesulfonate, bis(4-tert-butylphenyl)iodonium trifluoromethanesulfonate, triarylsulfonium compounds such as 4-(thiophenoxyphenyl)diphenylsulfonium hexafluoroantimonate, (4-bromophenyl)diphenylsulfonium trifluoromethanesulfonate and N-hydroxynaphthalimide trifluoromethanesulfonate and 2-(4-methoxystyryl)-4,6-bis(trichloromethyl)-1,3,5-triazine.

In particular, catalysts (K) which accelerate condensation between two silanol groups, between a silanol group and an alkoxysilyl group, between a silanol group and an Si—Cl group or between an alkoxysilyl group or Si—Cl group and water are used. Moreover, mixtures of various catalysts (K) can be used. The catalyst (K) is preferably used in a concentration of at least 10 ppm, more preferably at least 0.1% by weight, in each case based on the polymer blend, i.e. the reaction mixture. The catalyst (K) is preferably used in a concentration of not more than 20% by weight, more preferably not more than 10% by weight, and in particular not more than 2% by weight, in each case based on the polymer blend.

The invention further provides for the crosslinking of the resulting siloxanes selected from among the general formulae (4) and (7) by free-radical, cationic, anionic or coordination polymerization via their terminal double bonds, in particular in the radicals $R^9$.

Suitable crosslinking reagents are all reagents, additives, catalysts, in particular catalysts (K) or initiators (I), known to those skilled in the art. Preference is given to Lewis acids or compounds which form free radicals under the action of heat or by irradiation with UV light, or photo acid generators, i.e. compounds which decompose to generate a Brönsted acid on irradiation with high-energy radiation, for example UV light or electron beam.

Crosslinking can take place on the siloxanes selected from among the general formulae (4) and (7) during the polymerization or after the polymerization.

The ring opening and polymerization using the catalysts (K) can be carried out in various ways. Heating of the silanes or siloxanes with catalyst (K) for from 1 s to 48 h at from 5° C. to 300° C. Preference is given to a temperature of from 5° C. to 190° C.

Crosslinking using catalysts (K) and/or initiators (I) can be carried out in various ways. Heating of the silanes or siloxanes with catalyst (K) for from 1 s to 48 h at from 5° C. to 300° C. Preference is given to a temperature of from 5° C. to 190° C.

The silanes selected from among the general formulae (1) and (5) are preferably brought to a temperature of at least 50° C., in particular at least 80° C., to effect ring opening. Ring opening is preferably carried out at a temperature of not more than 180° C., in particular not more than 150° C.

Energy sources used for the ring opening and polymerization of the silanes selected from among the general formulae (1) and (5) and the crosslinking of the siloxanes selected from among the general formulae (4) and (7) by heating are preferably ovens, e.g. convection drying ovens, heating channels, heated rollers, heated plates, infrared radiators or microwaves.

The ring opening, polymerization and crosslinking can preferably also be effected by irradiation with ultraviolet light or electron beam.

Further examples of catalysts (K), in particular catalysts suitable for crosslinking, are Lewis acids, for example aluminum compounds such as aluminum(III) chloride, aluminum (III) isopropoxide, trimethylaluminum, boron compounds such as boron trichloride, and zirconium compounds such as Zr(IV) acetylacetonate.

Examples of initiators (I) which form free radicals under the action of heat or on irradiation with UV light are the thermal and photochemical polymerization initiators known to those skilled in the art, as are described, for example, in "Handbook of Free Radical Initiators" by E. T. Denisov, T. G. Denisova and T. S. Pokidova, Wiley-Verlag, 2003.

Examples of thermal initiators are tert-butyl peroxide, tert-butyl peroxopivalate, tert-butyl peroxo-2-ethylhexanoate, dibenzoyl peroxide, dilauroyl peroxide, azobisisobutyronitrile, tert-butyl peroxobenzoate or cumyl hydroperoxide. Examples of photoinitiators are benzophenone, 2-hydroxy-2-methyl-1-phenyl-1-propanone, 1-hydroxycyclohexyl phenyl ketone or methylbenzoyl formate.

Examples of photo acid generators are diaryliodonium compounds such as {4-[(2-hydroxytetradecyl)oxy] phenyl}phenyliodonium hexafluoroantimonate, diphenyliodonium nitrate, diphenyliodonium triflate, bis(4-tert-butylphenyl)iodonium p-toluenesulfonate, bis(4-tert-butylphenyl)iodonium trifluoromethanesulfonate, triarylsulfonium compounds such as 4-(thiophenoxyphenyl) diphenylsulfonium hexafluoroantimonate, (4-bromophenyl) diphenylsulfonium trifluoromethanesulfonate and N-hydroxynaphthalimide trifluoromethanesulfonate and also 2-(4-methoxystyryl)-4,6-bis(trichloromethyl)-1,3,5-triazine. The invention also provides the compounds of the general formulae (4), (5) and (7) and also the crosslinking products of the compounds of the general formulae (4) and (7).

The compounds of the general formulae (4) and (7) can be used for all purposes for which crosslinked siloxanes, in particular elastomeric siloxanes, silicone resins and crosslinked organic polymers are typically used.

In particular, the compounds of the general formulae (4) and (7) can be used for coating sheet-like textile structures, as polymer coating on paper, plastic films, packaging materials, mineral surfaces and metals.

The compounds of the general formulae (4) and (7) are likewise suitable as cast-making compositions or for producing moldings. The compounds of the general formulae (4) and (7) can likewise be used as adhesives, sealants and jointing materials or putty compositions.

All symbols in the above formulae in each case have their meanings independently of one another.

Unless indicated otherwise, all amounts and percentages are by weight, all pressures are 0.10 MPa (abs.) and all temperatures are 20° C.

The weight average molecular weight $M_w$ and number average molecular weight $M_n$ were determined by means of gel permeation chromatography (GPC) relative to a polystyrene standard, in THF, at 35° C., flow rate=1.0 ml/min and detection by means of RI (refractive index detector) on a column set PLgel-MIXED-C from Polymer Laboratories using an injection volume of 100 µl. The polydispersity PDI is the ratio $M_w/M_n$ of the weight average molecular weight $M_w$ and the number average molecular weight $M_n$. The determination of $M_n$ and $M_w$ is carried out by means of gel permeation chromatography (GPC) using a polystyrene standard, in THF, at 35° C., flow rate=1.0 ml/min and detection by means of RI (refractive index detector) on a column set PLgel-MIXED-C from Polymer Laboratories using an injection volume of 100 µl.

EXAMPLE 1

Polymerization and Crosslinking of 2,2,8,8-tetramethyl-1,7-dioxa-6-silaspiro[5.5]undecane 75.3 mg (0.18 mmol, 2 mol %) of diphenyliodonium triflate together with 15 ml of dry acetone are placed in a two-neck Schlenk tube made of fused silica. After 1 minute, 2.00 g (8.75 mmol, 1 eq) of 2,2,8,8-tetramethyl-1,7-dioxa-6-silaspiro-[5.5]undecane are added and after a further 5 minutes irradiation at 200-300 nm for 2 hours is commenced. Removal of the solvent gives a clear thin film which is insoluble in all conventional solvents.

EXAMPLE 2

Polymerization of 2,2,8,8-tetramethyl-1,7-dioxa-6-silaspiro[5.5]undecane 75.3 mg (0.18 mmol, 2 mol %) of diphenyliodonium triflate together with 15 ml of dry acetone are placed in a two-neck Schlenk tube made of fused silica. After 1 minute, 2.00 g (8.75 mmol, 1 eq) of 2,2,8,8-tetramethyl-1,7-dioxa-6-silaspiro-[5.5]undecane are added and after a further 5 minutes irradiation at 200-300 nm for 15 min is commenced. Removal of the solvent gives a soluble siloxane having a molar mass of $M_w$=150,000 g/mol and a PDI=1.61.

EXAMPLE 3

Copolymerization of 2,2,8,8-tetramethyl-1,7-dioxa-6-silaspiro[5.5]undecane with am-Si—OH-terminated siloxane In a fused silica Schlenk flask, 20 mg (0.088 mmol; 5 mol %) of 2,2,8,8-tetramethyl-1,7-dioxa-6-silaspiro[5.5]undecane are added to 4 g (1.77 mmol) of α,ω-Si—OH-terminated siloxane having an average length of 30 monomer units. 10 mg (0.023 mmol) of diphenyliodonium triflate in 3 ml of acetone are subsequently added and the mixture is irradiated at 200-300 nm for 2 hours. Immediately after irradiation, the solvent is removed, the polysiloxane is taken up in THF and the molar mass is determined by means of GPC: $M_w$=130,000 g/mol, PDI=2.17.

EXAMPLE 4

Copolymerization of 2,2,8,8-tetramethyl-1,7-dioxa-6-silaspiro[5.5]undecane with α,ω-Si—OH-terminated siloxane In a fused silica Schlenk flask, 20 mg (0.088 mmol; 5 mol %) of 2,2,8,8-tetramethyl-1,7-dioxa-6-silaspiro[5.5]undecane are added to 4 g (1.77 mmol) of α,ω-Si—OH-terminated siloxane having an average length of 30 monomer units. 9 mg (0.023 mmol) of triphenylsulfonium triflate in 3 ml of acetone are subsequently added and the mixture is irradiated at 200-300 nm for 2 hours. Immediately after irradiation, the solvent is removed, the polysiloxane is taken up in THF and the molar mass is determined by means of GPC: $M_w$=220,000 g/mol, PDI=3.5.

EXAMPLE 5

Reaction of α,ω-Si—OH-terminated siloxane with 2-isopropoxy-2,6,6-trimethyl-1,2-oxasilinane to give an end-functionalized siloxane In a Schlenk tube, 210 mg of 2-isopropoxy-2,6,6-trimethyl-1,2-oxasilinane (1.04 mmol, 4 eq) and 294 mg of α,ω-Si—OH-terminated siloxane having an average length of 10 monomer units (0.26 mmol, 1 eq) are added to 7.5 ml of benzene. The solution formed is stirred until the isopropoxy group can no longer be found in the 1H-NMR spectrum. The solvent is subsequently removed under reduced pressure.

This gives a clear, transparent oil.

$^1$H-NMR (500 MHz, $C_6D_6$, 300 K): δ [ppm]=1.84-1.78 (m, 2H), 1.73-1.68 (m, 2H), 1.36-1.34 (s, 6H), 1.26-1.25 (s, 6H), 0.79-0.68 (m, 4H), 0.59-0.44 (m, 4H), 0.34-0.18 (m, 96H).

$^{13}$C-DEPT135-NMR (126 MHz, $C_6D_6$, 300 K): δ [ppm]= 128.06, 40.93, 31.73, 29.55, 17.85, 12.97, 1.15, 0.86, 0.22.

$^{29}$Si-NMR (99 MHz, $C_6D_6$, 300 K): δ [ppm]=−19.30, −19.49, −19.57, −21.40, −21.78, −21.84, −21.95.

EXAMPLE 6

Polymerization of an End-Functionalized Siloxane

In a fused silica Schlenk flask, 2 mg (0.005 mmol) of triphenylsulfonium triflate in 3 ml of acetone are added to 1 g of the end-functionalized siloxane from example 5 and the mixture is irradiated at 200-300 nm for 2 hours. Immediately after irradiation, the solvent is removed. This gives a highly viscous oil which is soluble in conventional organic solvents such as THF.

EXAMPLE 7

Crosslinking Using Lewis Acids 6.05 g (2.94 mmol) of polysiloxane from example 3 are taken up in 70 ml of dichloromethane and admixed with 15.6 mg (0.11 mmol; 4 mol %) of $AlCl_3$ and stirred at room temperature for 4 hours. The solvent is subsequently removed under reduced pressure. A yellowish solid is formed. The product is insoluble in conventional organic solvents.

EXAMPLE 8

Crosslinking Using Peroxide 6.05 g (2.94 mmol) of polysiloxane from example 3 are taken up in 70 ml of dichloromethane and admixed with 28.4 mg (0.11 mmol, 4 mol %) of dibenzoyl peroxide, degassed three times and irradiated at 200-300 nm for 6 hours. The solvent is subsequently removed under reduced pressure.

This gives a highly viscous mass which can no longer be dissolved in conventional organic solvents.

EXAMPLE 9

Crosslinking Using Triphenylsulfonium Triflate 6.05 g (2.94 mmol) of polysiloxane from example 3 are taken up in 70 ml of dichloromethane and admixed with 45.3 mg (0.11 mmol; 4 mol %) of triphenylsulfonium triflate and irradiated with UV light at room temperature for 4 hours. The solvent is subsequently removed under reduced pressure. A yellowish solid is formed. The product is insoluble in conventional organic solvents.

EXAMPLE 10

Crosslinking of the Homopolymer Using $AlCl_3$ 3 g (13.13 mmol) of polysiloxane from example 2 are dissolved in 30 ml of dichloromethane and 70 mg (0.5 mmol, 4 mol %) of $AlCl_3$ are added and the mixture is stirred at room temperature for 2 hours. After half an hour, formation of flocs can be observed. The solvent is removed from the reaction solution. The polymer obtained is no longer soluble in conventional organic solvents.

The invention claimed is:
1. A process for the polymerization of oxasilacycles of the formulae (1) and (5)

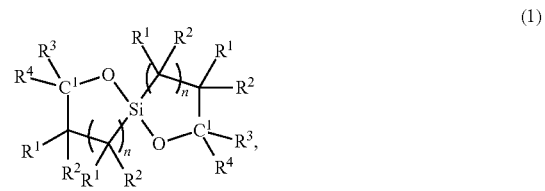

-continued

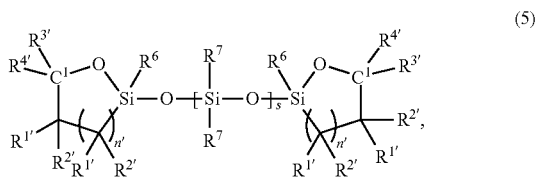
(5)

comprising polymerizing the oxasilacycles of the formulae (1) and/or (5), and optionally linear siloxanes of the formula (3) or cyclic siloxanes of the general formula (3a)

$$R-Si(R^7)_2O[Si(R^7)_2O]_oSi(R^7)_2-R, \quad (3)$$

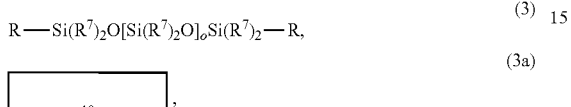
(3a)

in the presence of an acid catalyst K to form compounds of the formula (4)

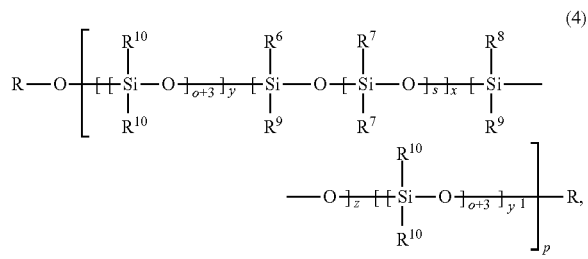
(4)

where

R are hydrogen, or an optionally substituted $C_{1-50}$ hydrocarbon radical or $C_{1-50}$ acyl radical, $R^1, R^2, R^{1'}, R^{2'}, R^{1''}, R^{2''}$ are hydrogen, halogen, cyano, OH, or an optionally substituted $C_{1-50}$ hydrocarbonoxy radical $C_{1-50}$, acyloxy radical, $C_{1-50}$ alkoxy radical or $C_{1-50}$ hydrocarbon radical, in which nonadjacent carbon atoms in each case are optionally replaced by heteroatoms N, O, P, and/or S, and where two or three of the radicals $R^1, R^2, R^{1'}, R^{2'}, R^{1''}, R^{2''}$ are optionally joined to one another, $R^3, R^4, R^{3'}, R^{4'}, R^{3''}$ are optionally substituted $C_{1-50}$ hydrocarbon radicals in which nonadjacent carbon atoms are optionally replaced by heteroatoms N, O, P, and/or S, or a high molecular weight radical, $R^{4''}$ are hydrogen, or optionally substituted $C_{1-49}$ hydrocarbon radicals in which nonadjacent carbon atoms are optionally replaced by heteroatoms N, O, P, and/or S, or are high molecular weight radicals, $R^6$ are optionally substituted $C_{1-50}$ hydrocarbon radicals in which nonadjacent carbon atoms are optionally replaced by heteroatoms N, O, P, and/or S, $R^7, R^{10}$ are optionally substituted $C_{1-10}$ hydrocarbon radicals having from 1 to 10 carbon atoms, $R^8$ are radicals $R^6$ or $R^9$, $R^9$ are radical of the formula (6)

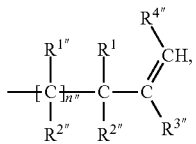
(6)

n, n', n'' are integers of at least 1, x, y, $y^1$ are each 0 or 1, z is an integer of at least 1, o is an integer of at least 0, p is an integer of at least 1 and s is an integer of at least 1.

2. The process of claim 1, wherein the compounds of the formula (4) are reacted in a subsequent step with an end-group-forming compound of the formula X-EG to give compounds of the formula (7)

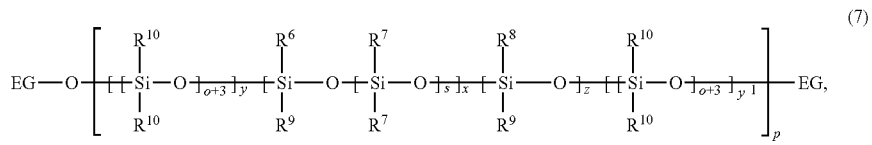
(7)

where

X is OH or halogen and

EG is a hydrocarbon or silyl group.

3. The process of claim 2, wherein the hydrocarbonoxy radicals or acyloxy radicals have from 1 to 6 carbon atoms.

4. The process of claim 2, wherein the hydrocarbon radicals $R^3, R^{3''}, R^{3'}, R^{4'}$ have from 1 to 12 carbon atoms and $R^{4''}$ is hydrogen or a hydrocarbon radical having from 1 to 12 carbon atoms.

5. The process of claim 2, wherein n and n' are each 2 or 3.

6. A compound having the formula (7) of claim 2, wherein at least one of y, $y^1$, or x is at least 1.

7. A crosslinked product of a compound of the formulae (7) of claim 2.

8. The process of claim 1, wherein the hydrocarbonoxy radicals or acyloxy radicals have from 1 to 6 carbon atoms.

9. The process of claim 8, wherein the hydrocarbon radicals $R^3, R^{3''}, R^3, R^4$ have from 1 to 12 carbon atoms and $R^{4''}$ is hydrogen or a hydrocarbon radical having from 1 to 12 carbon atoms.

10. The process of claim 1, wherein the hydrocarbon radicals $R^3, R^{3''}, R^{3'}, R^{4'}$ have from 1 to 12 carbon atoms and $R^{4''}$ is hydrogen or a hydrocarbon radical having from 1 to 12 carbon atoms.

11. The process of claim 1, wherein n and n' are each 2 or 3.

12. The process of claim 1, wherein $R^5$ is an alkyl group.

13. The process of claim 1, wherein $R^6$ is an alkyl group.

14. The process of claim 1, wherein $R^7$ and $R^{10}$ have from 1 to 6 carbon atoms.

15. The process of claim 1, wherein the catalysts (K) are Lewis acids and/or Brönsted acids.

16. A compound satisfying formula (5) of claim 1.

17. A crosslinked product of a compound of the formulae (4) of claim 1.

18. A compound having the formula (4) of claim 1, wherein at least one of y, $y^1$, or x is at least 1.

19. A process for preparing oxasilacycles of the formula (5)

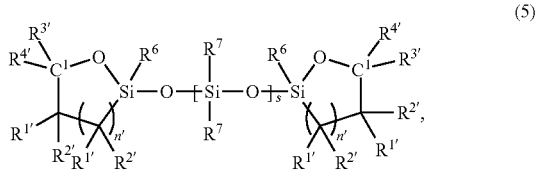

comprising reacting compounds of the formula (2),

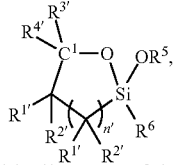

with siloxanes of the formula (3),

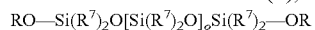

where
R is hydroxy, or an unsubstituted or substituted hydrocarbonoxy radical or acyloxy radical having from 1 to 50 carbon atoms,
$R^{1'}$, $R^{2'}$ are each hydrogen, halogen, cyano, OH, or an unsubstituted or substituted hydrocarbonoxy radical, acyloxy radical, alkoxy radical or hydrocarbon radical having from 1 to 50 carbon atoms, in which nonadjacent carbon atoms are optionally replaced by heteroatoms N, O, P, and/or S, and where two or three of the radicals $R^1$, $R^2$, $R^{1'}$, $R^{2'}$, $R^{1''}$, $R^{2''}$ are optionally joined to one another,
$R^{3'}$, $R^{4'}$ are each an unsubstituted or substituted hydrocarbon radical having from 1 to 50 carbon atoms, in which nonadjacent carbon atoms are optionally replaced by heteroatoms N, O, P, and/or S, or a high molecular weight radical,
$R^5$ is an unsubstituted or substituted hydrocarbon radical having from 1 to 10 carbon atoms,
$R^6$ is an unsubstituted or substituted hydrocarbon radical having from 1 to 50 carbon atoms, n which nonadjacent carbon atoms are optionally replaced by heteroatoms N, O, P, and/or S,
$R^7$ is an unsubstituted or substituted hydrocarbon radical having from 1 to 10 carbon atoms,
n' is an integer of at least 1,
o is an integer of at least 0 and
s is an integer of at least 1.

20. The process of claim 19, wherein the hydrocarbonoxy radicals or acyloxy radicals have from 1 to 6 carbon atoms.

21. The process of claim 19, wherein the hydrocarbon radicals $R^3$, $R^{3''}$, $R^{3'}$, $R^{4'}$ have from 1 to 12 carbon atoms and $R^{4''}$ is hydrogen or a hydrocarbon radical having from 1 to 12 carbon atoms.

22. The process of claim 19, wherein n and n' are each 2 or 3.

23. A process for crosslinking siloxanes of formula (4) and (7) comprising crosslinking by free-radical, cationic, anionic or coordination polymerization via terminal double bonds:

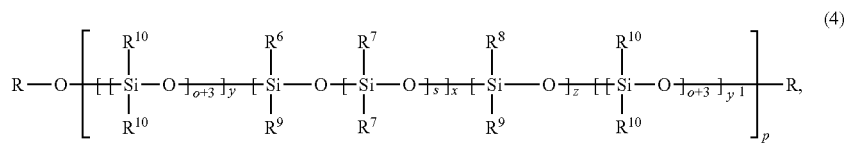

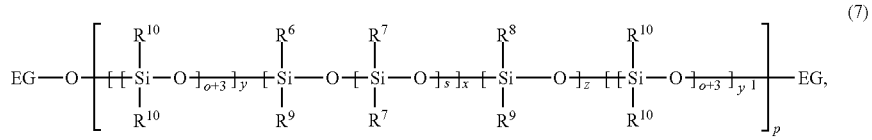

where
R are hydrogen, or an optionally substituted $C_{1-50}$ hydrocarbon radical or $C_{3-50}$ acyl radical,
$R^1$, $R^2$, $R^{1'}$, $R^{2'}$, $R^{1''}$, $R^{2''}$ are hydrogen, halogen, cyano, OH, or an optionally substituted $C_{3-50}$ hydrocarbonoxy radical $C_{1-50}$, acyloxy radical, $C_{1-50}$ alkoxy radical or $C_{1-50}$ hydrocarbon radical, in which nonadjacent carbon atoms in each case are optionally replaced by heteroatoms N, O, P, and or S, and where two or three of the radicals $R^1$, $R^2$, $R^{1'}$, $R^{2'}$, $R^{1''}$, $R^{2''}$ are optionally joined to one another,
$R^3$, $R^4$, $R^{3'}$, $R^{4'}$, $R^{3''}$ are optionally substituted $C_{1-50}$ hydrocarbon radicals in which nonadjacent carbon atoms are optionally replaced by heteroatoms N, O, P, and/or S, or a high molecular weight radical,
$R^{4''}$ are hydrogen, or optionally substituted $C_{1-49}$ hydrocarbon radicals in which nonadjacent carbon atoms are optionally replaced by heteroatoms N, O, P, and/or S, or are high molecular weight radicals,
$R^6$ are optionally substituted $C_{1-50}$ hydrocarbon radicals in which nonadjacent carbon atoms are optionally replaced by heteroatoms N, O, P, and/or S,
$R^7$, $R^{10}$ are optionally substituted $C_{1-10}$ hydrocarbon radicals having from 1 to 10 carbon atoms,
$R^8$ are radicals $R^6$ or $R^9$,
$R^9$ are radical of the formula (6)

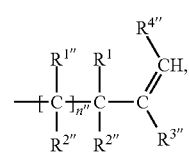

n, n', n'' are integers of at least 1,
x, y, $y^1$ are each 0 or 1,
z is an integer of at least 1, o is an integer of at least 0,
p is an integer of at least 1,
s is an integer of at least 1, and
EG is a hydrocarbon or silyl group.

24. A process for the polymerization of oxasilacycles of the formulae (1) and (5)

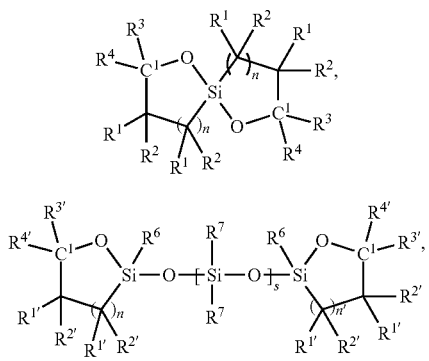

(1)

(5)

comprising polymerizing the oxasilacycles of the formulae (1) and/or (5), and optionally linear siloxanes of the formula (3) and/or cyclic siloxanes of the general formula (3a)

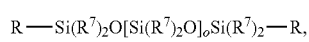

(3)

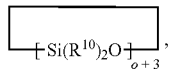

(3a)

in the presence of an acid catalyst K where
R are hydrogen, or an optionally substituted $C_{1-50}$ hydrocarbon radical or $C_{1-50}$ acyl radical, $R^1, R^2, R^{1'}, R^{2'}, R^{1''}, R^{2''}$ are hydrogen, halogen, cyano, OH, or an optionally substituted $C_{1-50}$ hydrocarbonoxy radical $C_{1-50}$, acyloxy radical, $C_{1-50}$ alkoxy radical or $C_{1-50}$ hydrocarbon radical, in which nonadjacent carbon atoms in each case are optionally replaced by heteroatoms N, O, P, and/or S, and where two or three of the radicals $R^1, R^2, R^{1'}, R^{2'}, R^{1''}, R^{2''}$ are optionally joined to one another, $R^3, R^4, R^{3'}, R^{4'}, R^{3''}$ are optionally substituted $C_{1-50}$ hydrocarbon radicals in which nonadjacent carbon atoms are optionally replaced by heteroatoms N, O, P, and/or S, or a high molecular weight radical, $R^{4''}$ are hydrogen, or optionally substituted $C_{1-49}$ hydrocarbon radicals in which nonadjacent carbon atoms are optionally replaced by heteroatoms N, O, P, and/or S, or are high molecular weight radicals, $R^6$ are optionally substituted $C_{1-50}$ hydrocarbon radicals in which nonadjacent carbon atoms are optionally replaced by heteroatoms N, O, P, and/or S, $R^7, R^{10}$ are optionally substituted $C_{1-10}$ hydrocarbon radicals having from 1 to 10 carbon atoms,

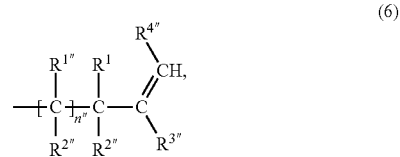

(6)

n, n' are integers of at least 1,
o is an integer of at least 0,
s is an integer of at least 1,
to form a polymeric product.

* * * * *